United States Patent [19]

Ricci

[11] Patent Number: 5,133,208

[45] Date of Patent: Jul. 28, 1992

[54] APPARATUS FOR THE PREPARATION AND EXECUTION OF TESTS ON THE SEDIMENTATION RATE OF ORGANIC LIQUIDS AND OTHER

[75] Inventor: Antonio Ricci, Siena, Italy

[73] Assignee: Diesse Diagnostica Senese s.r.l., Milan, Italy

[21] Appl. No.: 502,166

[22] Filed: Mar. 29, 1990

[30] Foreign Application Priority Data

Apr. 5, 1989 [IT] Italy ................. 9392 A/89

[51] Int. Cl.[5] .............................. G01N 15/04
[52] U.S. Cl. .................... 73/61.66; 494/10; 494/16
[58] Field of Search .......... 73/61.4, 64.1; 494/10, 494/16, 20, 33

[56] References Cited

U.S. PATENT DOCUMENTS

| | | | |
|---|---|---|---|
| 3,677,071 | 7/1972 | Martin | 73/61.4 |
| 3,882,716 | 5/1975 | Beiman | 73/61.4 |
| 3,980,227 | 9/1976 | Witty et al. | 494/16 X |
| 4,118,974 | 10/1978 | Nozaki et al. | 73/61.4 |

Primary Examiner—Hezron E. Williams
Assistant Examiner—Joseph W. Roskos
Attorney, Agent, or Firm—McGlew and Tuttle

[57] ABSTRACT

The apparatus of the present invention can be used to measure sedimentation rate of samples. The samples are placed in a sample rotor and are rotatable about a sample rotor axis. The sample rotor axis can be moved into two positions. In one position the sample rotor axis is substantially horizontal and in the other position the sample rotor axis is substantially vertical. Rotation of the sample rotor about the sample rotor axis causes stirring of the samples when the sample rotor axis is horizontal. When the sample rotor axis is substantially vertical settling of the samples occur. Step rotation of the sample rotor brings the samples to a reading means in order to analyze the samples. An optical signal sensor moves along the sides of the test tubes for measuring the sedimentation rate.

11 Claims, 3 Drawing Sheets

APPARATUS FOR THE PREPARATION AND EXECUTION OF TESTS ON THE SEDIMENTATION RATE OF ORGANIC LIQUIDS AND OTHER

FIELD AND BACKGROUND OF THE INVENTION

The object of the invention is an apparatus for the preparation and execution of tests on the sedimentation velocity of previously treated organic liquids which must be stirred within test tube-like containers. Such apparatus used for the so-called sedimentation rate test and other similar uses.

SUMMARY AND OBJECTS OF THE INVENTION

The purpose of the invention is to provide a simple, reliable apparatus able to quickly carry out the various operation steps. These and other purposes and advantages will be evident by a reading of the following description.

Substantially, the apparatus according to the invention comprises in combination: on a base structure, a holder oscillating about a horizontal axis between two limit positions; on said holder, a rotor able to rotate about a rotation axis orthogonal to said horizontal axis; on said rotor, a crown of seats for test tubs inclined and symmetrically disposed around said rotation axis; and in a reading station, reading means along the test tube that reaches the station by intermittent displacements of the rotor when disposed with its axis upwardly directed. When the holder is in its lowered position the phase of stirring the liquids within the test tubes is carried out. When the holder is in its vertical condition the sedimentation measurements are carried out, and also reapeted (in kinetic mode), on each test tube.

The apparatus comprises a motor on said oscillating holder to drive the rotor into operation with the rotation axis in substantially horizontal condition for the stirring of the test tubes, and into intermittent operation with the rotation axis in substantially vertical position to bring the test tubes to the reading station in succession. It is not excluded that, with certain inclinations of the test tubes, the sedimentation or decantation be accelerated whenever allowed by the kind of test to be carried out.

The apparatus may comprise a motor for the displacement of the rotor holder between the two positions, with means for the controlling and stopping thereof in the reached positions.

The reading means may comprise guide means for slide member able to slide parallel to the test tube in the reading position; on the slide members being provided members for emitting and receiving an optical signal which crosses the test tube during the reading stroke. A suitable motorization—for example, a flexible member driven by wheels and a driving pulley—is provided to cause the slide to perform the reading sweep. The slide may be apt to reach an end-position of the reading stroke and reading cycle of the test tube, in which said emitting and receiving members are placed outside of the trajectory of the test tubes in transit through the reading station.

The test tubes may be advantageously of the type having prismatic and preferably flat walls with their major dimension being placed in the diametral plane of the rotor axis, and the test tubes may be disposed to be engaged within the seats by friction clamps and made to converge towards the axis of rotation with their closed ends, thereby resulting inclined of approximately 18° to the axis of rotation; the oscillating holder is able to reach two positions in which the rotation axis of the rotor is respectively horizontal for the stirring phase, and vertical for the reading phase.

The apparatus may be combined with a computerized system with a program for performing the operating cycle allowing reapeted readings (in kinematic mode) and the introduction of correction factors for example (and especially) in relation to the temperature of the work environment.

The invention will be better understood by the following description and the attached drawing, which shows a practical, non limiting example of the same invention.

DETAILED DESCRIPTION OF THE PREFERRED EMBODIMENT

Figure 1:
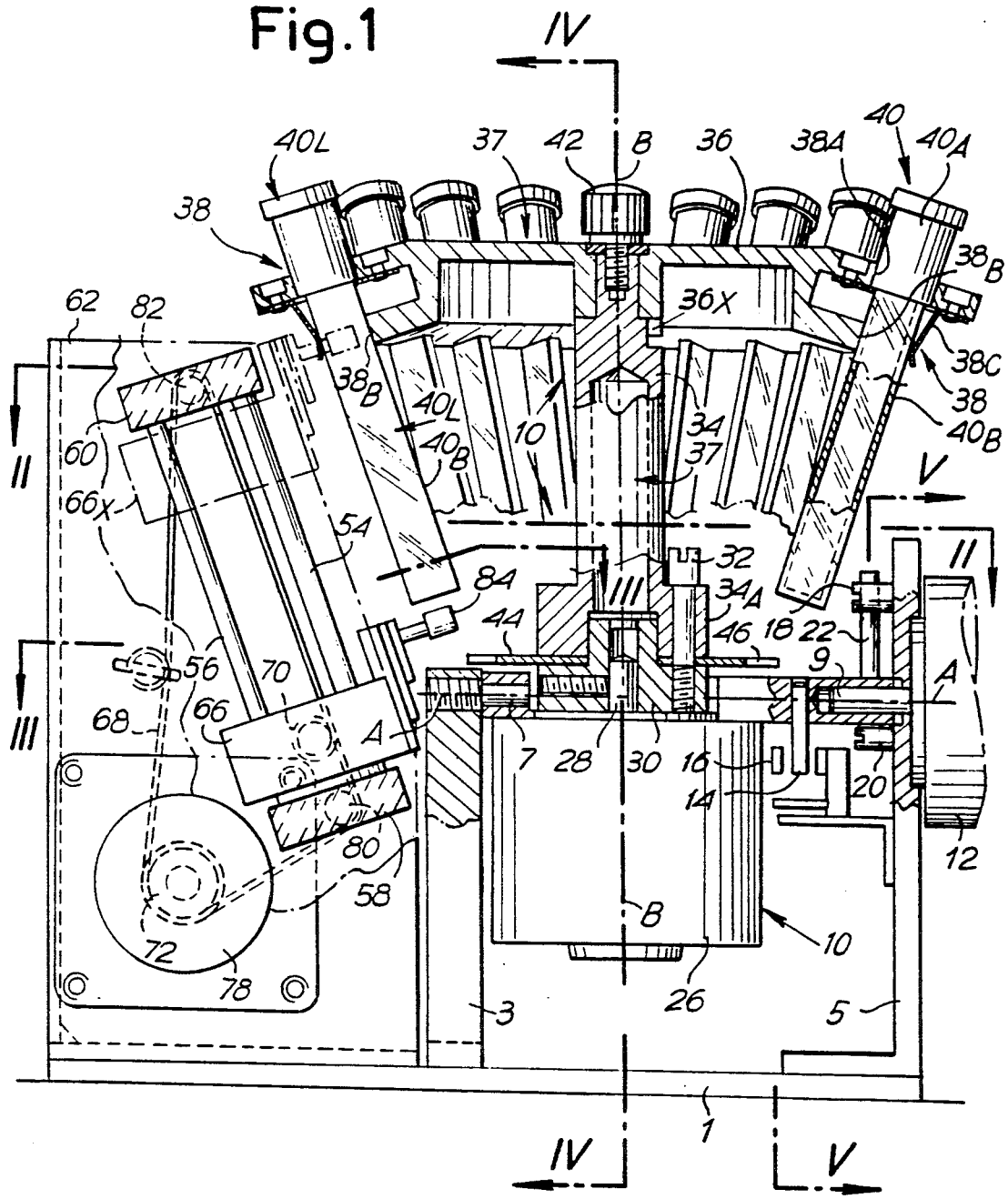
FIG. 1 shows a vertical sectional view of the apparatus with the rotor axis in a vertical arrangement.
Figure 2:
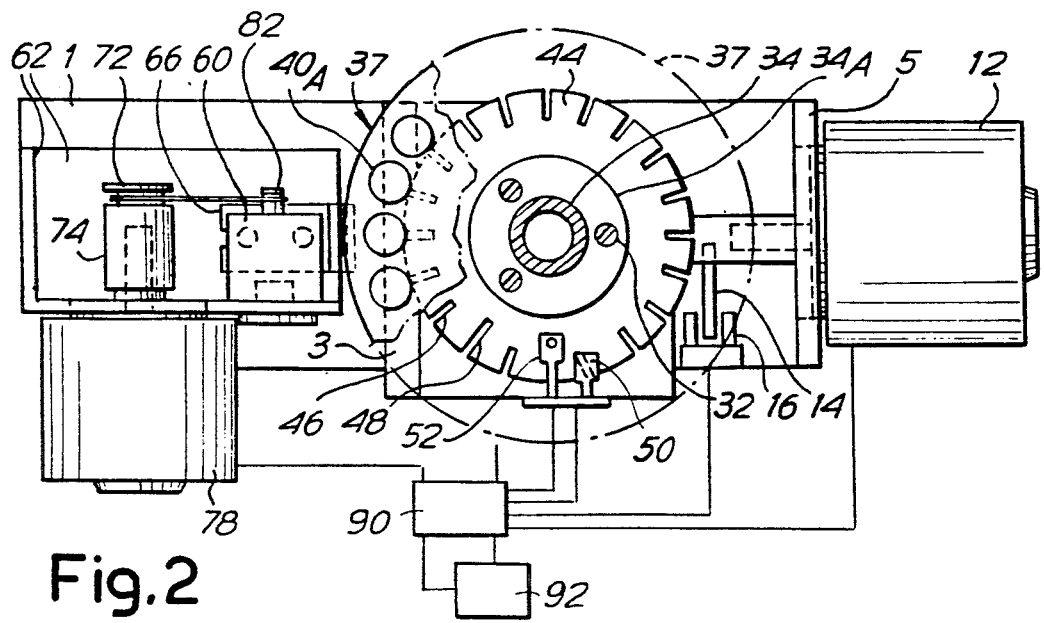
FIGS. 2 and 3 show two horizontal sectional views taken on lines II—II and III—III of FIG. 1.
Figure 3:
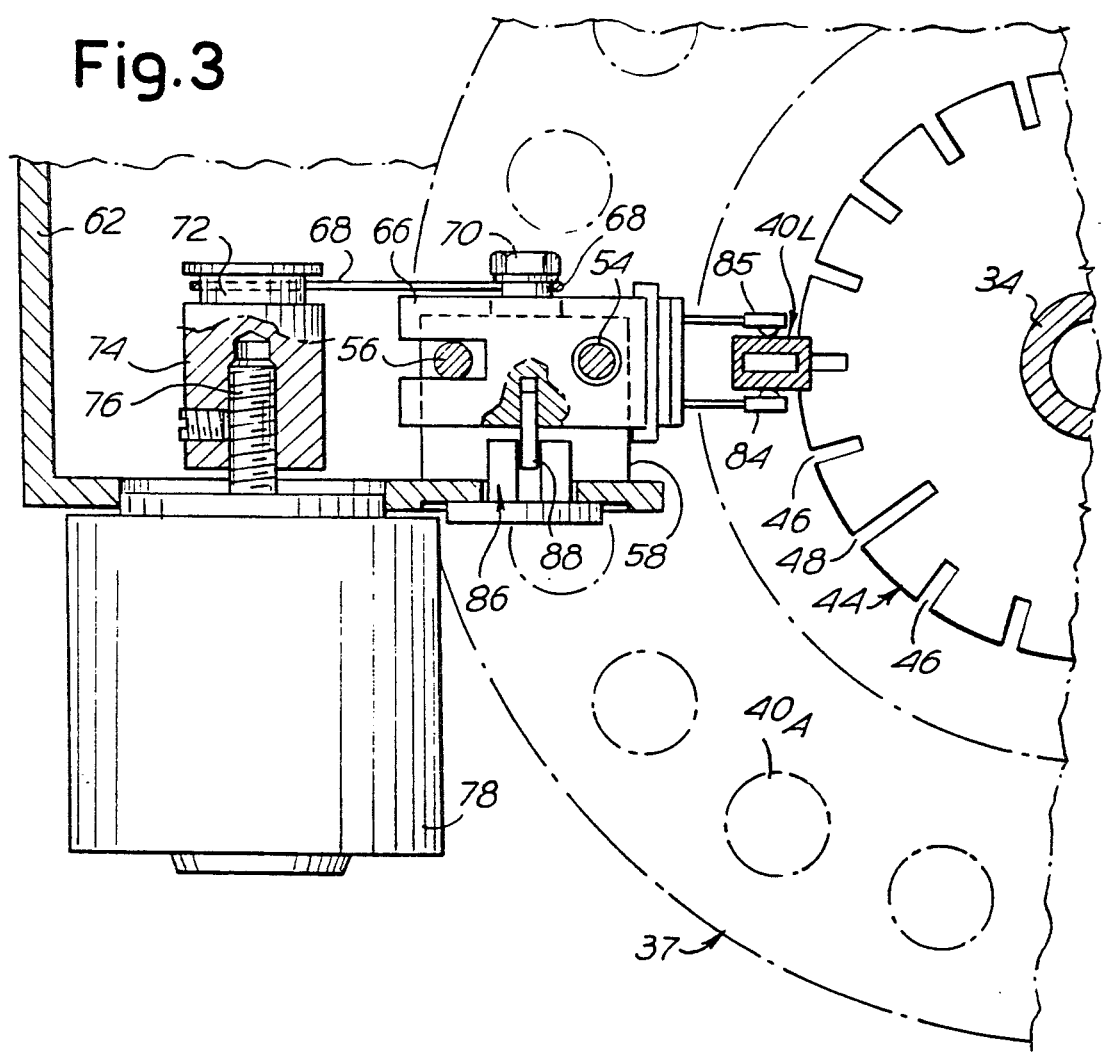
Figure 4:
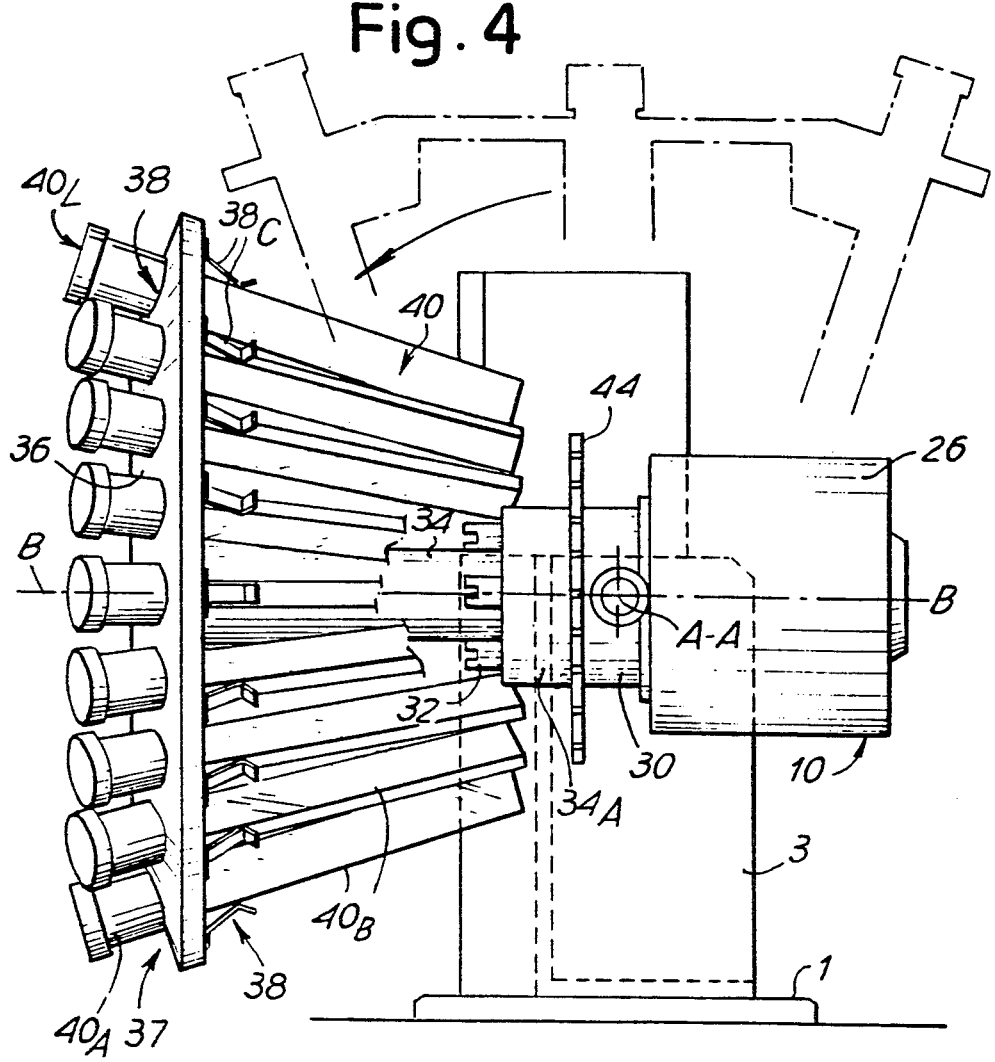
FIG. 4 shows a section on line IV—IV of FIG. 1, with the rotor axis in horizontal arrangement.
Figure 5:
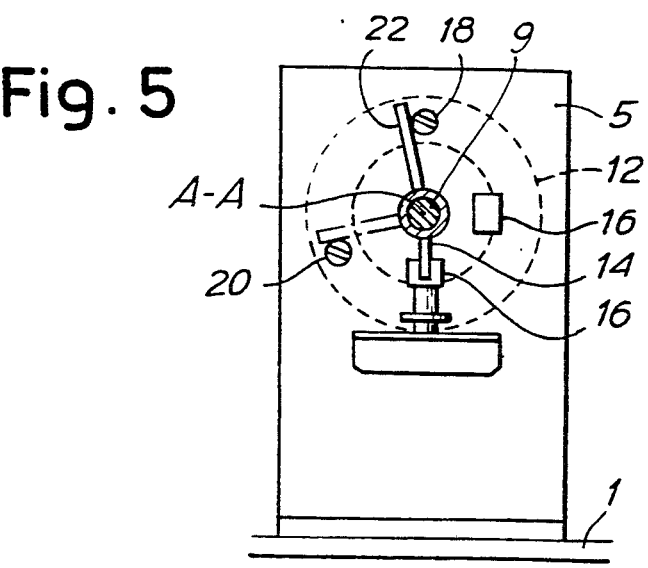
FIG. 5 shows a local section on line V—V of FIG. 1.

According to what is illustrated in the attached drawings, numeral 1 indicates a base structure on which two supports 3 and 5 are provided for two pivot pins 7 and 9, and which are aligned according to, and on, an oscillation axis A—A for a holder 10 oscillating about said horizontal axis A—A. The pin 9 may be represented by the rotation axis of a base motor 12 mounted on the support 5 and able to move the holder between two positions orthogonal to each other. The other positions can be detected by suitable detection means, which for example comprising projection 14 radially extending on the holder 10 orthogonally to the oscillation axis A—A, and optical sights 16 for the detection of the position of this projection 14. Pawls 18 and 20 may also be provided, with which a further projection 22, also radially projecting with respect to axis A—A of the oscillating holder 10, is able to co-act. The oscillating holder 10 comprises a sample motor 26 with output shaft having an axis B—B orthogonal to the horizontal oscillation axis A—A of said holder 10. To an output shaft 28 of sample motor 26 a body 30 is solidly connected. A column 34, 34A is connected to the body 30 by means of screw 32 or other equivalent means. The column supports, at the end opposite to the motor 26, a disc or plate 36 provided with seats for housing the test tubes are samples. The members 28, 30, 34, 36 make up a sample rotor 37 borne by the oscillating holder 10 and making up a substantial portion of such holder. The disc or plate 36 is provided with seats generally indicated by 38, circumferentially distributed about the B—B axis of the sample rotor 37. Each seat 38 may consist of a through hole 38A and of a bearing shoulder 38B, facing a pressure spring 38C which stems from a laminar crown engaged around hole 38A. Each test tube 40 may be inserted into the seat 38 and being elastically pressed against shoulder 38B by the relevant spring 38C. The test tubes 40 are advantageously of the type having a head 40A with access opening apt to be closed by a suitable shutter and a lengthwise body which is prismatically developed and has flat cross-section as indicated in 40B. The major median is in the diametral plane passing through the axis of the test tube P and through the axis B—B of rotor 37. The axis of each test tube in the above mentioned diametral plane is inclined to the B—B axis at an angle suitable for facilitating the operations to be performed by the apparatus, for example, for facilitating the sedimentation by an inclination in the order of about 18°, which is an inclination apt to accelerate the sedimentation for the assessment of the so-called sedimentation rate of organic liquids. The disc or plate 36 with seats 38 can be readily replaced for various reasons including that of changing the inclination of the test tubes axis with respect to the axis B—B of rotor 37 of the holder 10, and/or for changing the type of test tube to be used for the analysis. For the assembly and disassembly of the disc or plate 36 there may be provided a screw member 42 which is engaged to the end of column 34 to fix the disc or plate thereto at a predetermined position by means, for example, of a datum tooth 36X received into a corresponding seat of column 34.

The holder 37 rotating about the axis B—B, which is also the axis of the sample step-by-step motor 26, is provided with a disc 44 engaged between the base 34A of column 34 and the body 30 mounted on shaft 28. This disc 44 is provided with slots 46 having a disposition corresponding to that of seats 38 and thus of test tubes 40. One of the slots, which extend radially from the edge of disc 44, is deeper than those indicated by 46 and is designated by 48, in order to make up a datum (or reference) for the zero position. The step-by-step motor 26 of the rotor 37 of the holder 10 (and through it, the position of rotor 37) is controlled by detecting of slots 46 and slot 48 by means of the optical sights 50 and 52, the first controlling all the slots 46 and the slot 48, while the sight 52 controls only the slot 48 to indicate the zero position of rotor 37.

As can be seen from the drawing, the test tubes are symmetrically inclined with respect to the axis B—B of rotor 37, the ends of the prismatic bodies 40 converging towards said axis B—B.

In a side position with respect to the rotor unit there is provided a station for the reading of a test tube which takes up the position 40L when it is placed in the reading station. In correspondence with the reading station there is a reading system along the body 40B of the test tube located at position 40L.

To carry out the above mentioned reading, which is an optical reading across the body 40B of the test tube at position 40L, there is provide a mobile slide parallel to the development of body 40B of said test tube in position 40L. To achieve this, a guide system is provided comprising two guide stems 54 and 56 extending between two connection bodies 58 and 60. The connection bodies 58 and 60 are fixed to a square bracket 62 which is engaged to the base 1. On the guide means represented by the stems 54 and 56 there is made to slide a slide 66 which can be displaced by means of a flexible cable 68 anchored by a clamp 70 to the slide 66. The flexible cable is wound with several turns over a drum 72 formed by a body 74 solid to the shaft 76 of a motor 78 fixed to the square bracket 62. The flexible cable 68 is suitably driven by pulleys 80 and 82 borne by supports 58 and 60. In this way, by means of motor 78, it is possible to cause the slide 66 to perform reciprocating travels on the guides 54 and 56. In the side view (FIG. 1), the slide 66 is shown at the lower travel end with solid lines and at the upper travel end with broken lines and with reference 66X. The slide 66 carries two terminal 84, 85 facing each other which make up the emitting and receiving means for an optical signal which crosses the body 40B of the test tube at the reading position 40L during the travels of slide 66. When the slide is at the lower position shown with solid line in FIG. 1, the two terminals 84, 85 are placed below the body 40B of the test tube located at 40L, so that they do not interfere with this test tube nor with all the other test tubes when the rotor 37 rotates around the axis B—B to bring the test tubes in succession to the reading position 40L. On the square support 62 there may be placed a group 86 making up a sensor for detecting of the position of slide 66 which, to this end, is provided with a projection 88 able to transit between the two sight lugs of group 86.

The operation of the apparatus is as follows. In order to load the test tubes, the holder 10 is disposed with its axis B—B in vertical position to allow the insertion of the test tubes into the seats 38 with the head 40A turned upwards. The work cycle is then started and base motor 12 rotates to bring the holder 10 with its axis B—B into horizontal position. The sample motor 26 is then actuated to start the rotation of rotor 37 and thus determining the stirring of test tubes 40. By rotating about the axis B—B which is horizontally disposed, the test tubes 40 are made to perform a cyclic oscillating and rotating movement which causes the uniform stirring of all the liquids contained in the test tubes 40. The holder 10 is then made to rotate about the axis A—A to bring the holder 10 back with the rotor axis B—B in vertical position and then start the sedimentation phase. This phase, owing to a phenomenon well known to those skilled in the art, is accelerated due to the fact that the test tubes are inclined to the vertical. In certain cases, and possibly with test tubes disposed, for example, with an upwards and outwards inclination (by replacing the disc or plate 36 and providing a suitable different positioning of the reading system), another effect may be caused similar to the one previously described. At the end of a sedimentation period it is possible to perform a reading or, during the sedimentation phase, it may be possible to also performed a series of readings in kinetic mode, in order to assess the sedimentation degree of liquids held in the test tubes. To achieve this, the rotor 37 is made to rotate intermittently through motor 26 (which may be of step-by-step type), thereby causing the test tubes 40 to reach in succession the reading position 40L. The slide 66 being, during each displacement, having its terminals 84, 85 in the lower position inwarder to avoid any interference with the test tubes. Upon each stop of motor 26, and thus when the next test tube reaches position 40L, the motor 78 causes the slide 66 to perform a lifting travel and then a lowering travel. From position 66 to position 66X and back again to position 66 respectively, a reading is taken through terminals 84 and 85, across the body 40B of the next test tube at position 40L, thereby assessing the transparency, during the displacements, by means of data suitably processed and stored in memory. The readings of the various test tubes can be made in very short times. Since it is possible to repeat more cyclic readings in sequence for all the test tubes and thus obtaining repeated readings on each test tube, there may be obtained reading data in kinetic mode. This being particularly advantageous for certain results in the research on the sedimentations of organic liquids.

The apparatus may be associated to a computerized unit 90 for the computation, storing and then printing of the obtained data. The computerized unit may be driven by systems 92 for the control of data from the individual test tubes by utilizing signals obtainable through slots 46 and the zero slot 48, in order to obtain a safe classification of the various data achieved from the single test tubes. To the computerization unit there may also be combined a unit for the correction of data, to account for the temperatures of the environment in which the apparatus operates, without thereby any need for air conditioning of the same environment and thereby reaching a high accuracy with no influence from the sudden changes of temperature the environment may be exposed to.

I claim:

1. An apparatus for performing sedimentation rate tests, the apparatus comprising:
 a base;
 a holder rotatably connected to said base, said holder being rotatable between a first position and a second position;
 a sample rotor rotatably connected to said holder, said sample rotor being rotatable about an axis substantially orthogonal to an axis of rotation of said holder, said sample rotor having a plurality of seats for holding samples and being rotated with said holder; and
 reading means for analyzing each sample as each sample arrives at said reading means, said reading means being connected to said base, and rotary movements of said sample rotor, when said holder is in said second position, moving the samples toward said reading means.

2. An apparatus in accordance with claim 1, wherein: said plurality of seats are symmetrically disposed and orientated around said axis of said sample rotor, to separately deliver each of the samples to said reading means, said plurality of said seats hold the samples at an inclination with respect to said axis of said sample rotor.

3. An apparatus in accordance with claim 1, further comprising:
 a sample motor means for rotating and stirring the samples when said holder is in said first position and for intermittent rotation of the sample rotor in said second position of said holder for bringing the samples in succession to said reading means, said sample motor means being connected to said sample rotor and mounted on said holder.

4. An apparatus in accordance with claim 1, further comprising:
 a base motor means for displacement of said holder between said first and second positions, and for stopping and controlling said holder in said first and second positions.

5. An apparatus in accordance with claim 1, wherein: said seats are associated with friction clamp means for holding the samples inclined at substantially 18 degrees to said axis of said sample rotor; and said first position of said holder places said axis of said sample rotor substantially horizontal for stirring the samples, and said second position of said holder places said axis of said sample rotor substantially vertical for moving the samples to said reading means.

6. An apparatus in accordance with claim 1, further comprising:
 a computer means for programming movement of said holder, said sample rotor and said reading means, said computer means having a mode for analyzing the samples in a kinetic mode and for accounting for temperature and other changes.

7. An apparatus for performing sedimentation rate tests, the apparatus comprising:
 a base;
 a holder rotatably connected to said base, said holder being rotatable between a first position and a second position;
 a sample rotor rotatably connected to said holder, said sample rotor being rotatable about an axis substantially orthogonal to an axis of rotation of said holder, said sample rotor having a plurality of seats for holding samples; and
 reading means for analyzing each sample as each sample arrives at said reading means, said reading means being connected to said base, and rotary movements of said sample rotor, when said holder is in said second position, moving the samples toward said reading means, said reading means has optical signal means for said analyzing of the sample, said reading means having guide means for moving said optical signal substantially parallel along one of the samples to be analyzed when said one of the samples to be analyzed is in a reading position.

8. An apparatus in accordance with claim 7, wherein: said optical signal means has emitting means for emitting an optical signal on one side of the sample and receiving means for receiving said optical signal on another side of said sample; and said reading means has a motorization means for moving said optical signal means along said guide means.

9. An apparatus in accordance with claim 7, wherein: said optical signal means is movable into a position outside a trajectory of the samples, said trajectory being caused rotations of said holder and said sample rotor.

10. An apparatus in accordance with claim 8, wherein:
 said motorization means has a flexible cable driven by pulleys and a motorized drum to move said optical signal means.

11. An apparatus in accordance with claim 8, wherein:
 said samples are held in test tubes having a prismatic shape for distortion free transmission of said optical signal.

* * * * *